United States Patent [19]

Alexandrovich, Sr. et al.

[11] Patent Number: 5,345,811
[45] Date of Patent: Sep. 13, 1994

[54] FLUID DENSITY SENSOR AND SYSTEM

[75] Inventors: George Alexandrovich, Sr., Commack; Stanley Sporn, Oceanside; Stanley Wood, Middle Island, all of N.Y.

[73] Assignee: Parker Hannifin Corporation, Cleveland, Ohio

[21] Appl. No.: 861,664

[22] Filed: Apr. 1, 1992

[51] Int. Cl.$^5$ ............................................. G01N 9/10
[52] U.S. Cl. .................................................. 73/32 A
[58] Field of Search ............... 73/32 A, 24.05, 61.49, 73/61.75

[56] References Cited

U.S. PATENT DOCUMENTS

| | | | |
|---|---|---|---|
| 3,282,084 | 11/1966 | Banks | 73/32 A |
| 4,114,423 | 9/1978 | Wenger | 73/24.05 |
| 4,240,285 | 12/1980 | Langdon | 73/32 A |
| 4,283,936 | 8/1981 | November | 73/32 A |
| 4,429,564 | 2/1984 | Ikeda et al. | 73/32 A |
| 4,526,480 | 7/1985 | Ward | 73/32 A |
| 4,809,499 | 3/1989 | Dyer | 73/32 R |
| 4,876,880 | 8/1989 | Dyer | 73/32 R |
| 4,890,480 | 1/1990 | Young | 73/32 A |
| 4,909,068 | 3/1990 | Miura et al. | 73/32 A |
| 4,922,745 | 5/1990 | Rudkin et al. | 73/32 A |
| 4,961,345 | 10/1990 | Tsuruoka et al. | 73/32 A |

Primary Examiner—John E. Chapman
Attorney, Agent, or Firm—Ralph E. Jocke

[57] ABSTRACT

A sensing element and system for determining the density of fuel housed in the tank of an aircraft, includes sensing element (10). The sensing element has a disc shaped member (20) extending through a wall (16) of the sensor body. The sensor body also encloses a chamber (14) containing dry nitrogen at a pressure of one atmosphere. Electromagnetic driving coils (24) are electrically actuated to cause member 20 to vibrate in its resonant frequency in four quadrants with a node along an axis (22) corresponding to the wall of the sensor and a second node axis (42). Pickup coils (26) in the sensor body sense displacement of the disc shaped member in a location of maximum displacement. Fluid surrounding the sensing element causes mass loading of the exposed portion of the disc shaped member and changes its resonant frequency. The changes in resonant frequency along with values determined through calibration are used by a processor (44) to calculate the density of the fluid.

13 Claims, 2 Drawing Sheets

FLUID DENSITY SENSOR AND SYSTEM

TECHNICAL FIELD

This invention relates to aircraft fuel systems. Specifically, this invention relates to a sensor and system for measuring the density of aircraft fuel housed in a tank.

BACKGROUND ART

In jet aircraft applications, fuel is traditionally measured by weight rather than by volume. This is because the volume of a given amount of fuel varies substantially with changes in fuel temperature experienced by an aircraft during flight. The weight of the fuel provides a more reliable indication than fuel volume of how long the plane engine(s) can run on the amount of fuel remaining.

Prior art aircraft fuel systems have included sensors and systems that estimate fuel density from the dielectric constant of the fuel or the fuel temperature. From the estimate of fuel density, the weight of fuel remaining is calculated. Unfortunately, the accuracy of systems that estimate fuel weight based on the dielectric constant or temperature are limited. This is because the relationship between fuel density and the dielectric constant, as well as the relationship between fuel density and temperature has limited accuracy, especially when batch to batch fuel variations are considered.

Other types of prior art fuel density measuring systems include sensors which determine density from the frequency of a vibrating member. Typical systems of this type utilize a vibrating cylinder as a resonator which is caused to vibrate at a resonant frequency by electromagnetic forces. The vibrating cylinder, when immersed in the fuel, changes its resonant frequency in accordance with the density of the fuel. From the changes in resonant frequency, the density is estimated.

When units of this type are used in aircraft, a means of compensation must be provided to account for changes in resonant frequency that occur due to head pressure of fuel above the sensor and gas pressure above the fuel. In conventional sensor designs, pressure effects act on one side of the vibrating cylinder which is immersed in the fuel. The opposite side of the cylinder is typically housed in a vacuum in a sealed enclosure which protects the electromagnetic coils used to vibrate the cylinder. Compensating for pressure effects complicates the sensing system and increases the probabilities of inaccuracy (under vibration, for example).

Thus, there exists a need for a sensor and system that more accurately measures the density of aircraft fuel under conditions normally experienced during flight by a jet aircraft, is easier to use and economical to manufacture.

DISCLOSURE OF INVENTION

It is an object of the present invention to provide a sensor and system that may be used to reliably and accurately measure the density of a fluid.

It is a further object of the present invention to provide a sensor and system that may be used to measure the density of a fluid at temperatures and pressures experienced by jet aircraft fuel under all aircraft operating conditions.

It is a further object of the present invention to provide a sensor and system that may be used to measure the density of a fluid that is minimally affected by changes in fluid viscosity.

It is a further object of the present invention to provide a sensor and system that may be used to measure the density of jet fuels and other liquids of various types.

It is a further object of the present invention to provide a sensor and system for measuring the density of a fluid that is economical to manufacture and use.

Further objects of the present invention will be made apparent in the following Best Modes for Carrying Out Invention and the appended claims.

The foregoing objects are accomplished in the preferred embodiment of the invention by a novel sensor and system that may be used to measure the density of the fluid. The sensor is immersed in the fluid and has a sensing element that includes a body with an internal chamber. A wall separates the internal chamber from the fluid surrounding the sensor body. The chamber inside the body is evacuated or in some embodiments filled with a non-reactive gas at a convenient pressure.

A flat disc shaped member is mounted in the body with one-half of the member extending inside the chamber and the other half extending outside the body in the fluid whose density is to be measured. The disc shaped member is mounted in the wall so that it is held along an axis through its center. The wall is relatively thin in the area where the disc is mounted so that bending effects of the disc are transmitted between the interior and exterior portions of the member, and vibrations are not substantially dampened.

A pair of electromagnetic driving coils are mounted inside the chamber. The driving coils are mounted at an angle approximately 45° to the axis along which the disc shaped member is held in the wall. Each driving coil is positioned near an outer periphery of the disc shaped member.

A pair of electromagnetic pickup coils are mounted inside the chamber at an angle approximately 90° from the driving coils. The pickup coils are also mounted adjacent the periphery of the member.

The driving and pickup coils are electrically connected to phase lock loop circuitry. The circuitry is designed to vibrate the disc shaped member at a resonant frequency. In the preferred form of the invention, the member vibrates in four equal quadrants called the "sting ray" mode. In this mode of vibration, there is a node where the disc experiences no displacement which extends along the axis where the disc shaped member is held to the wall. A further node extends along a second node axis. The second node axis extends through the center of the disc perpendicular to the axis at which the disc is held to the wall. As a result, each quadrant vibrates 180° out of phase with the adjacent quadrants.

The density of the fluid to be measured creates a mass loading effect on the external part of the disc shaped member. This changes the member's resonant frequency in a manner that is correlated to the density of the fluid. The phase lock loop circuitry insures that the disc shaped member always vibrates in the sting ray mode despite the change in resonant frequency due to mass loading. From the resonant frequency of the disc, a processor connected to the sensor calculates the density of the fluid based on established physical relationships.

In the preferred embodiment of the invention, the sensor body has a thermoelastic coefficient that is approximately the negative of the thermoelastic coefficient of the disc shaped member in the normal operating range of the sensor. As a result, changes in temperature have only a small impact on the accuracy of the sensor. In situations where greater accuracy is required, this impact is minimized by correction factors based on temperature measurement that are used in calculating fluid density. Further, because the disc shaped member has both of its sides immersed in the fluid, it is not affected by pressure effects while the plane is in flight. The disc shaped member in the preferred embodiment is also tapered to a pointed edge about its periphery. This reduces the sensitivity of the transducer to changes in viscosity of the fluid whose density is to be measured.

BEST MODES FOR CARRYING OUT INVENTION

Figure 1:
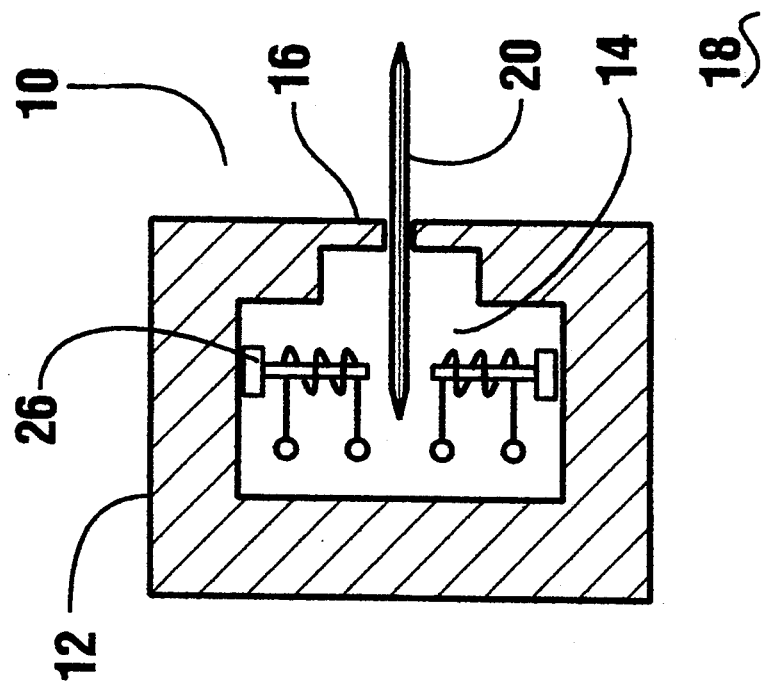
FIG. 1 is a cross sectional view of the fluid density sensing element of the present invention.

Referring now to the drawings and particularly to FIG. 1, there is shown therein the fluid density sensing element of the preferred form of the present invention generally indicated 10. The sensing element has a body 12 with an internal chamber 14. A wall 16 separates chamber 14 from the fluid which surrounds the sensing element which is generally indicated 18.

Figure 2:
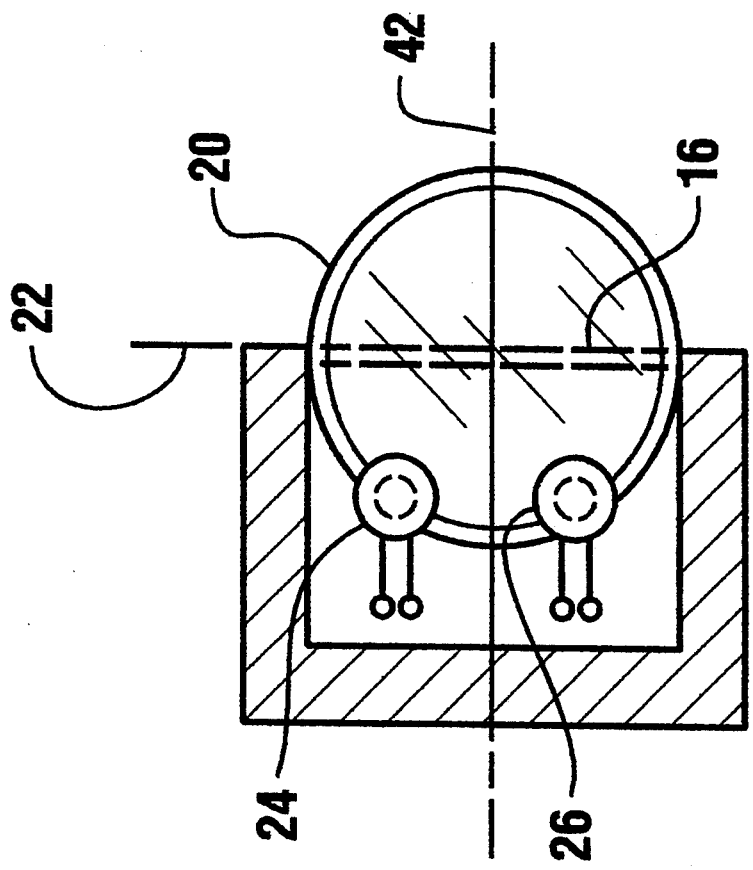
FIG. 2 is a top view of the disc shaped member driving coils and pickup coils of the sensing element.

A disc shaped member 20 extends through a wall 16 and is fixably mounted therein. In the preferred form of the invention, the disc is welded in place in the wall. As shown in FIG. 2, wall 16 is a straight wall and is coaxial with a first axis 22 through the center of disc shaped member 20. Wall 16 is thinned in the area where member 20 passes therethrough as shown in FIG. 1.

Figure 3:
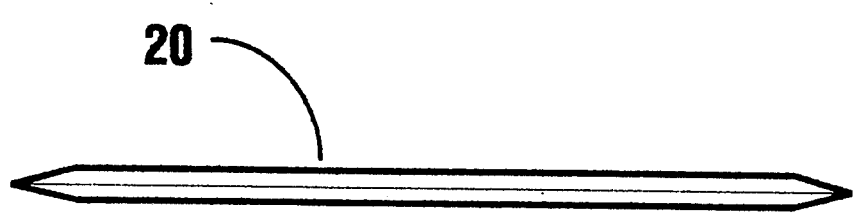
FIG. 3 is a side view of the disc shaped member.

Disc shaped member 20 is a relatively thin flat disc of unitary construction. As shown in FIG. 3, it is tapered about its periphery to a pointed edge. In the preferred form of the invention, the disc shaped member is tapered about its full circumference at about a 12° included angle. The disc is approximately 1.25 in. in diameter and is made of Ni-Span-C nickel iron alloy, which is a magnetic material. Of course, in other embodiments of the invention, other materials and dimensional relationships may be used.

A pair of driving coils 24 (only one of which is shown in FIG. 2) are mounted inside chamber 14. In the preferred embodiment, driving coils are mounted in opposed fashion such that there is one on each side of member 20. In other embodiments, both driving coils may be on one side of the disc and both pick up coils may be on the other side of the disc, or only one driving coil may be used, or other combinations may be used. The driving coils are positioned adjacent an outer periphery of member 20. The driving coils are conventional electromagnetic coils which are comprised of a magnet and pole piece, and a coil as schematically shown in FIG. 1. As is shown more clearly in FIG. 2, driving coils 24 are positioned approximately 45° from axis 22. As later explained, the driving coils 24 are used to impart motion to member 20 at a first location on the disc adjacent the driving coils.

A pair of pickup coils 26 are also mounted inside chamber 14 of the sensing element. Pickup coils 26 are conventional electromagnetic coils similar to driving coils 24. The pickup coils are positioned adjacent a second location on the disc which is approximately 90° from the position of the driving coils. As later explained, pickup coils 26 are used to measure the displacement of member 20 at the second location.

In the preferred form of the invention, the body 12 of the sensor element 10 is made from stainless steel material which is nonmagnetic. Chamber 14 is filled with dry nitrogen at one atmosphere in the preferred embodiment. In other embodiments chamber 14 may be evacuated or filled with another non-reacting gaseous material.

Figure 4:
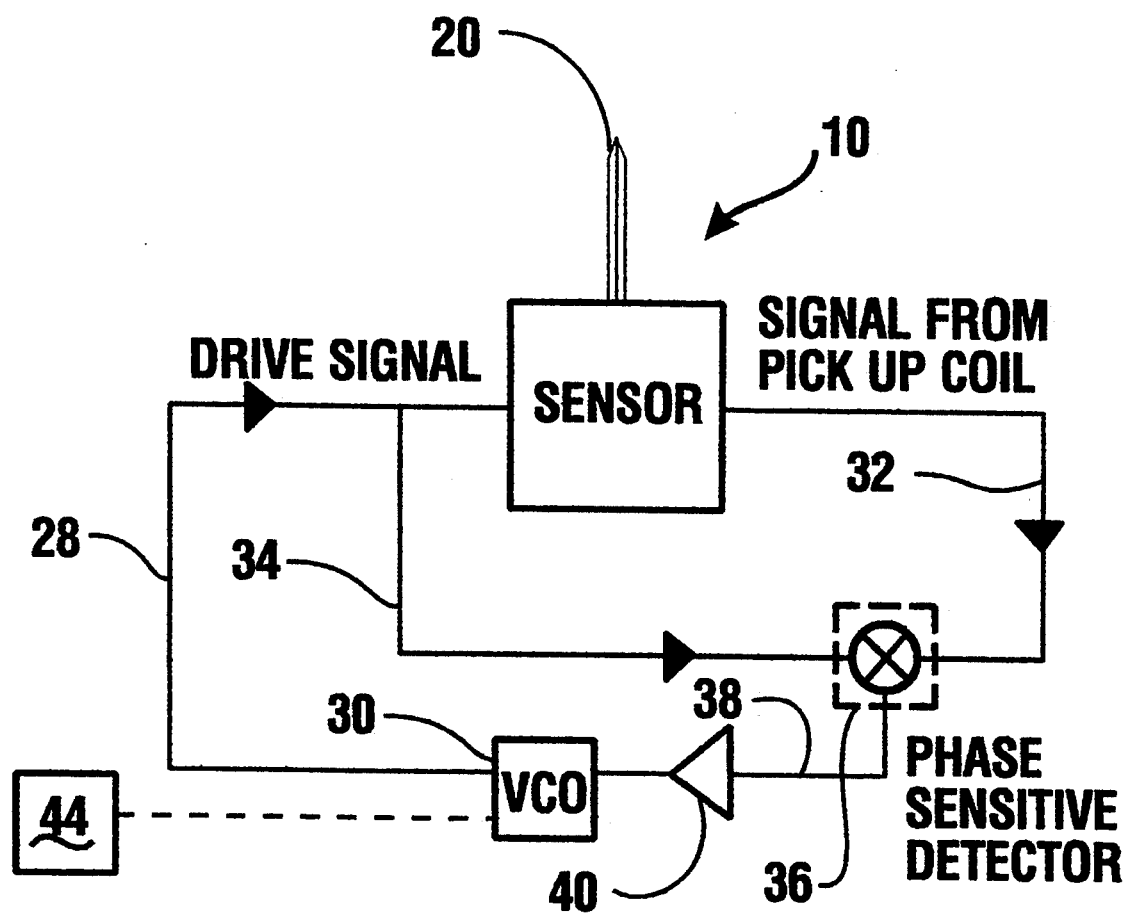
FIG. 4 is a schematic of the phase lock loop circuitry and processor of the system of the present invention.

In the preferred form of the invention, the sensing element is connected to phase lock loop circuitry of the type schematically shown in FIG. 4. In other embodiments a standard oscillator sustaining amplifier may be used, or a computer can determine resonant frequency, in the proper mode, by frequency search. The driving coils are driven electrically by a signal on line 28. A regularly oscillating current is delivered on line 28 from a voltage controlled oscillator generally indicated 30.

Pickup coils of a sensor element are connected to a line 32. Line 32 is connected to a phase separation detector element generally indicated 36. A line 34, which is in connection with line 28 provides the driving signal to the phase separation detector. The phase separation detector 36 provides an output signal on line 38 which is amplified in amplifier 40 and fed back to the voltage controlled oscillator 30.

The phase lock loop circuitry is designed to maintain a constant phase angle separation between the driving signal and the signals produced by the pickup coils. This constant phase separation insures that the disc shaped member 20 is always maintained in vibration at its resonant frequency, and in the desired mode of vibration.

In the preferred form of the invention, member 20 is made to vibrate in its resonant frequency wherein it vibrates at four equal quadrants with adjacent quadrants 180° out of phase. This is called the "sting ray" mode. In this resonant frequency, there is a node which is an area where the disc experiences no displacement extending along first axis 22. There is a further node along a second axis 42 (see FIG. 2). The second node axis 42 extends through the center of the disc shaped member and perpendicular to axis 22. In the sting ray mode, areas of maximum displacement occur between the nodes. These areas of maximum displacement include the first location adjacent the driving coils and the second location adjacent the pickup coils, as well as in the quadrants of the disc which are immersed in the fluid.

The fluid 18 surrounding the sensor element acts on both sides of member 20 that are external of the body. This creates a mass loading and effects the resonant frequency at which the member will vibrate in the sting ray mode. The density of the fluid may be mathematically determined from the resonant frequency as hereafter described. As shown in FIG. 4, the frequency of oscillator 30 is in electrical connection with a processor 44 which carries out the calculations that determine fluid density.

It is known that the resonant frequencies of a disc are determined by its geometry and are affected by the constructional details of the mounting of the disc. Particularly significant to achieving accurate density measurements in the sensing element of the present invention is the stiffness and damping effects caused by the mounting of the disc shaped element to the wall and the decoupling effects between the portion of the disc shaped member extending inside the chamber of the sensing element and the portion extending outside the element. The sting ray mode, as previously described, is particularly useful for the sensing element as it minimizes the adverse effects of the required rigid mounting of the disc shaped member.

It is known from vibration analysis that the first order natural frequencies for a circular plate in half disc configuration may be determined from the following equation:

$$f_n = \frac{K}{2\pi\sqrt{12}} \sqrt{\frac{Eg}{(1-\mu^2)\rho}} \left(\frac{h}{a^2}\right) \quad (1)$$

In this equation, the symbols represent the following quantities:

$f_n$ = frequency
K = a constant depending on plate geometry, boundary conditions, and mode.
Thus:
K = $K_1$ = a constant for Sting Ray Mode
K = $K_2$ = a constant for Flipper* Mode
K = $K_3$ = a constant for See Saw** Mode
K = $K_n$ = for other modes
E = Disc Modulus of Elasticity
g = Acceleration of Gravity ≈ 386 in/sec$^2$
$\rho$ = Density of Disc Material
$\mu$ = Poisson's Ratio ≈ 0.33
h = disc thickness
a = disc diameter
r = disc radius = a/2

Flipper Mode has one diametral mode aligned along the line of axis 22 with both halves of the disc in phase.

See Saw Mode is similar to Flipper Mode except that both halves of the disc are vibrating 180° out of phase.

Both the inner and outer halves of the disc shaped member are separately resonant and would have approximately the same natural frequency if the disc were suspended in air along the natural node along axis 22. However, in the sensor element, they are coupled through the center of the member and the thinned area of the wall. As a result, the total disc shaped member will exhibit dual frequencies of resonant vibration if the coefficient of coupling ($K_c$) is greater than critical. The coefficient of critical coupling has the following relationship:

$$K_c \sim \frac{1}{\sqrt{Q_1 Q_2}} \quad (2)$$

Where
$Q_1$ = Q of outer half disc
$Q_2$ = Q of inner half disc

As a result, it is expected that for the disc shaped member used in the sensor element of the present invention, peaks will be exhibited both above and below the resonant frequency for the half disc sting ray mode, as well as above and below other half disc modes in which the coefficient of coupling is greater than critical.

To determine the density of the fluid surrounding the sensing element, the following physical relationships apply. Because the sensing element is immersed in the fluid, an effective mass of the disc shaped member can be modelled and may be taken to be:

$$M_{Eff} = Vol_D \rho_D + Vol_c \rho_F \quad (3)$$

Where:
$M_{Eff}$ = effective mass of the vibrating disc (i.e. the disc mass that determines the vibration frequency in the sense of $$f = \sqrt{K/M}$$

$Vol_D$ = volume of disc
$\rho_D$ = density of disc material
$Vol_c$ = a "control volume" to be defined
$\rho_F$ = density of fluid In equation 3, the control volume ($Vol_c$) represents the quantity of the fluid impinging on the external portion of disc shaped member 20 that contributes to the mass loading of the vibrating disc.

The effective density of the disc shaped member may be taken to be:

$$\rho_{eff} = \frac{M_{Eff}}{Vol_D} = \rho_D + \left(\frac{Vol_c}{Vol_d}\right)\rho_F \quad (4)$$

$\rho_{EFF}$ = effective density of vibrating disc

Thereafter, by substituting the effective density of the vibrating disc shaped member as determined from equation 4, the natural frequency is determined to be:

$$f_n = B \sqrt{\frac{Eg}{(1-\mu^2)\left[\rho_D + \left(\frac{Vol_c}{Vol_D}\right)\rho_F\right]}} \left(\frac{h}{a^2}\right) \quad (5)$$

Where $B = \frac{K}{2\pi\sqrt{12}}$

By substituting, the natural frequency of the disc shaped member may then be stated in terms of the natural frequency in a vacuum as follows:

$$f_n = \frac{f_o}{\sqrt{1 + \left(\frac{Vol_C}{Vol_d}\right)\frac{\rho_F}{\rho_D}}} \quad (6)$$

$f_o$ = frequency in vacuum

The density of the fluid may be then solved in terms of the period of vibration of the natural frequency ($1/f_n$)

$$\rho_F = -\left(\frac{Vol_D}{Vol_C}\right)\rho_D + \left(\frac{Vol_D}{Vol_C}\right)\rho_D f_o^2 T_n^2 \quad (7)$$

Where $T_n = \frac{1}{f_n}$

Rewriting the equation provides the following relationships:

$$\rho_F = K_o + K_2 T_n^2 \quad (8)$$

and $$K_o = -\left(\frac{Vol_D}{Vol_C}\right)\rho_D$$

-continued $$K_2 = \left(\frac{Vol_D}{Vol_C}\right)\rho_D f_o^2$$

AND $$\frac{K_2}{K_o} = -f_o^2$$

It should be noted that the bias term ($K_o$) is always negative.

As a result, by determining the natural frequency of a particular sensing element in fluids over a range of densities, the constant coefficient terms necessary to calculate fluid density as a function of frequency of vibration in the sting ray mode, may be determined for the particular sensor. In the preferred form of the invention, each sensor is calibrated in this manner after manufacture. From Applicant's experience, no two sensor elements are identical.

In the preferred form of the invention, the constant bias and slope terms ($K_o$) and ($K_2$) respectively are stored in a read only member chip (ROM) associated with the sensing element. The information on these constants is then multiplexed onto the disc frequency and transmitted to the processor where the density is calculated in accordance with equation 8. However, in other embodiments, the constants may be stored in program resistors, or in other memory, in connection with processor 44.

In sensing the density of aircraft fuels, there is always a concern about bubbles in the fluid that may reside on the disc shaped member. In the preferred embodiment of the invention, the amplitude of member vibration is chosen to be small so that the pressure effects in the fuel caused by the vibration do not produce forces which tend to attract bubbles to the disc shaped member.

A significant advantage associated with the preferred form of the sensing element and system of the present invention is that it is not significantly impacted in its output by pressure effects. This is because the portion of the disc shaped member immersed in the fluid is inherently balanced to fluid pressure. There are equal areas on both sides of the exposed flat disc shaped surfaces. Because the pressure forces are balanced, the frequency variation due to pressure is negligible. As a result, the sensor and system of the present invention are accurate over the full range of pressures experienced in the fuel tanks of the aircraft.

A further advantage of the preferred embodiment of the present invention is that the impact in its accuracy by viscosity effects is minimized. The viscosity effects are minimized by the tapered periphery of the disc shaped member. The tapering of the periphery of disc shaped member also increases the value of the slope constant ($K_2$) in equation 8, which minimizes the relative value of the error and the other terms when the density is calculated.

The preferred embodiment of the invention is also made to be substantially self compensating for temperature. This is done by having the thermoelastic coefficient of the disc shaped member be controlled through cold working and heat treatment. The thermoelastic coefficient of the stainless steel body of the element is inherently negative. By working the disc shaped member so that its thermoelastic coefficient is the opposite of that of the body material, the effects may be effectively canceled across the operating range of the sensor. This is readily done through the use of the materials previously mentioned in the preferred embodiment.

In other embodiments of the invention, temperature effects may be dealt with in other ways. One way of dealing with temperature effects is to calibrate the sensing element over a wide range of temperatures. A temperature sensor may be then incorporated into the element. Temperature signals sent to the processor may be used by the processor to automatically correct for temperature changes. Of course a combination of the approach of making the disc and body thermally self compensating, combined with full calibration and correction achieves effective results.

Thus, the fluid density sensing element and system of the present invention achieve the above stated objectives, eliminate difficulties encountered in the use of prior devices and systems, solve problems and obtain the desirable results described herein.

In the foregoing description, certain terms have been used for brevity, clarity and understanding, however, no unnecessary limitations are to be implied therefrom because such terms are for descriptive purposes and are intended to be broadly construed. Moreover, the descriptions and illustrations herein are examples and the invention is not limited to the exact details shown or described.

Having described the features, discoveries and principles of the invention, the manner in which it is constructed and operated, and the advantages and useful results obtained; the new and useful structures, devices, elements, arrangements, parts, combinations, systems, equipment, operations and relationships are set forth in the appended claims.

We claim:

1. Apparatus for measuring density of a fluid, comprising:
    a sensing element adopted for immersion in said fluid;
    said element having a body, said body enclosing a chamber, said chamber bounded by a wall separating said fluid external of said body and said chamber;
    a disc shaped vibrating member, said vibrating member fixed to said wall along a first axis through a center thereof, a first portion of said member extending in said chamber and a second portion of said member extending in said fluid;
    means for exciting resonant frequency vibration of said disc shaped member wherein said member has a linear node extending along said first axis; and
    means for sensing frequency of vibration of said disc shaped member whereby said frequency of vibration is representative of the density of said fluid.

2. The apparatus according to claim 1 wherein in said resonant frequency of vibration of said member, said member vibrates in four quadrants and has a second linear node extending along a second axis, said second axis extending through the center of said member perpendicular to said first axis.

3. The apparatus according to claim 2 wherein said chamber contains dry nitrogen at a pressure of one atmosphere and said member is comprised of magnetic material, and wherein said means for exciting vibration includes means for moving said member at a first location inside said chamber through electromagnetic effects, and wherein said means for sensing frequency includes means for sensing movement of said member in a second location inside said chamber through electromagnetic effects.

4. The apparatus according to claim 3 wherein said first and second locations are disposed at generally equal and opposed angular displacements from said second node axis.

5. The apparatus according to claim 4 wherein said first and second locations are adjacent a periphery of said member and are disposed at generally 90° to one another.

6. The apparatus according to claim 5 wherein said periphery of said member is inwardly tapered about a circumference of said member.

7. The apparatus according to claim 6 wherein said body is comprised of a first material having a first thermoelastic coefficient, and said member is comprised of a second material having a second thermoelastic coefficient, and wherein said first thermoelastic coefficient is generally the negative of the second thermoelastic coefficient in the operating range of said sensing element.

8. The apparatus according to claim 7 wherein said wall of said body is relatively thin adjacent said first axis of said member.

9. The apparatus according to claim 8 wherein said exciting means includes phase lock loop circuit means for achieving sustained vibration of said member at said resonant frequency.

10. The apparatus according to claim 9 wherein said first material is stainless steel and said second material is Ni-Span-C nickel iron alloy.

11. The apparatus according to claim 10 wherein said taper of said member is generally about a 12° included angle emanating from said periphery of said member.

12. The apparatus according to claim 11 wherein said member has a diameter through said center to said periphery, and a constant thickness across said member to said taper of generally 1/25th of said diameter.

13. The apparatus according to claim 12 wherein said diameter of said member is generally 1.25 in., and said fluid is jet fuel.

* * * * *